United States Patent [19]

Thomas et al.

[11] 4,351,784
[45] Sep. 28, 1982

[54] CORONA TREATMENT OF PERFORATED FILM

[75] Inventors: Paul E. Thomas; Garland E. Raley, both of Terre Haute, Ind.

[73] Assignee: Ethyl Corporation, Richmond, Va.

[21] Appl. No.: 216,269

[22] Filed: Dec. 15, 1980

[51] Int. Cl.³ .............................................. B29D 27/00
[52] U.S. Cl. ......................................... 264/22; 264/26
[58] Field of Search ............................ 264/22, 25, 26; 425/174.8 E

[56] References Cited

U.S. PATENT DOCUMENTS

| | | | |
|---|---|---|---|
| 2,763,759 | 9/1956 | Mito et al. | 264/25 |
| 3,054,148 | 9/1962 | Zemmerli | |
| 3,394,211 | 7/1968 | MacDuff | 264/154 |
| 3,471,597 | 10/1969 | Schirmer | 264/25 |
| 3,880,966 | 4/1975 | Zimmerman et al. | 264/25 |
| 3,929,135 | 12/1975 | Thompson | 128/287 |

Primary Examiner—James B. Lowe
Attorney, Agent, or Firm—Donald L. Johnson; John F. Sieberth; Paul H. Leonard

[57] ABSTRACT

A perforated thermoplastic film with tapered capillaries which has an increased liquid flow rate through the tapered capillaries and a method for making such a film. The method includes subjecting a perforated thermoplastic film having tapered capillaries to a corona discharge treatment sufficient to increase the flow rate of liquid through said perforated film.

The film made in accordance with the invention has a much higher liquid transmission rate than the perforated film of the prior art. Furthermore, the film may be treated with a corona discharge continuously as the film is being formed and perforated.

10 Claims, 3 Drawing Figures

CORONA TREATMENT OF PERFORATED FILM

BACKGROUND OF THE INVENTION

This invention relates to the manufacture of thermoplastic films. More particularly, this invention relates to thermoplastic films having minute perforations on a regularly arranged pattern over substantially the entire surface of the film which have increased liquid flow rates through their perforations and are useful in making sanitary and apparel structures or assemblies, and particularly for making infant diapers.

Many thermoplastic films of different strengths, characteristics, colors, and dimensions are produced for a multitude of products. Perforated films have a multiplicity of regularly spaced apertures which allow permeation of liquid and air or other fluids. Such films can be used as a component of disposable composition garments for sanitary apparel purposes, such as napkins, diapers, or for hospital pads, bed or sleeping bag linings, and the like. In such composite structures, an exterior layer of film having the desired properties is provided which would be adjacent to the skin in a composite garment, and the garment would also include a filler layer or layers of absorbent fibrous material.

A particular class of perforated film is described by Thompson, U.S. Pat. No. 3,929,135, issued Dec. 30, 1975. Thompson teaches an absorptive structure with a top layer of perforated film characterized by having a series of regular spaced small apertures in the form of tapered capillaries of certain dimensions ranges. In the finished article, these are directed inwardly to be in intimate contact with an absorbent fibrous material layer. The smooth side of the perforated film is thus in use in contact with the skin. Film as described by Thompson, in garment structure as outlined, maintains a dry and comfortable condition, even after transmission of fluids to the absorbent layer by the combined effects of the absorption and the resistance to back flow as a result of the relative length and surface properties of the tapered capillaries.

One method for making film with tapered capillaries on one side thereof is shown in U.S. Pat. No. 3,054,148, issued Sept. 18, 1962, to Zimmerli. In this patent heated film is supported by a perforated screen and a vacuum applied to the underside of the perforated screen. Holes are pulled in the film in the direction of the vacuum beneath the screen thereby forming tapered capillaries in the film.

An alternative technique for forming tapered capillaries is disclosed in U.S. Pat. No. 3,394,211, issued July 23, 1968, to McDuff. In the McDuff process the perforation technique comprises applying a blast of heated air to create a pressure differential across a perforated forming surface, conditions being appropriate to cause a rupture at a desired point.

Furthermore, film may be perforated by a variety of other means including mechanical perforation by pins or the like, and by electrical means such as corona discharge. U.S. Pat. No. 3,471,597 discloses a method for perforating a film by corona discharge and U.S. Pat. No. 3,880,966 discloses a method of increasing the permeability of a film with corona discharge. However, some, if not all, of such films do not have tapered capillaries.

An object of the present invention is to increase the flow of liquids through a perforated film having tapered capillaries.

THE INVENTION

In accordance with the present invention there is provided a perforated thermoplastic film with tapered capillaries which has an increased liquid flow rate through the tapered capillaries and a method for making such a film. The method includes subjecting a perforated thermoplastic film having tapered capillaries to a corona discharge treatment sufficient to increase the flow rate of liquid through said perforated film.

The film made in accordance with the invention has a much higher liquid transmission rate than the perforated film of the prior art. Furthermore, the film may be treated with a corona discharge continuously as the film is being formed and perforated.

DESCRIPTION OF THE PREFERRED EMBODIMENTS

Figure 1:
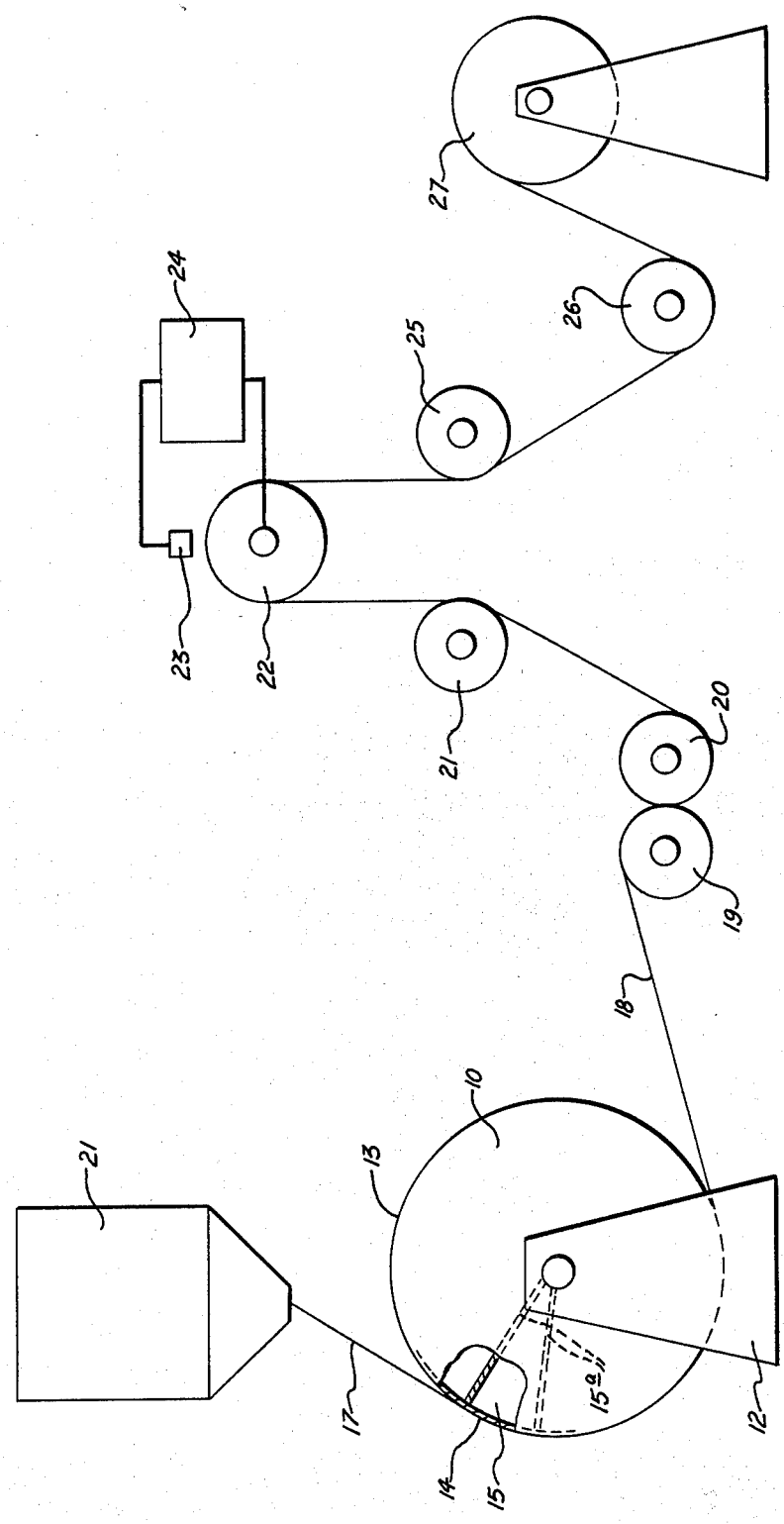
FIG. 1 is a schematic elevational view showing the inter-relationship of the principle pieces of equipment employed in carrying out the process.

Referring to FIG. 1, an apparatus for carrying out the process of the invention includes a rotary cylindrical drum 10 supported at each end by a centrally disposed axle 11 supported by means of stationary axle supports 12. The cylindrical surface 13 of drum roll 10 is highly perforated to allow air to pass therethrough. The molding element or screen 14 is mounted around the surface 13 of drum 10 and is adapted to rotate with the drum 10.

Element 14 may be formed as an integral unit adapted to be slipped on drum 10 from an end thereof or it may be wrapped around the drum 10 and then secured thereto in any suitable manner. For purposes of rotating drum 10, a gear drive may be employed which is adapted to mesh with gearing provided on the drum element itself or a pulley drive may be connected to the drum by means of caps provided on the ends thereof. As shown in FIG. 1, a vacuum chamber 15 is utilized to create a pressure differential between the respective surfaces of the thermoplastic sheet to cause the plasticized sheet to flow into the perforations provided in the molding element 14 and therefore perforate the sheet.

Figure 2:
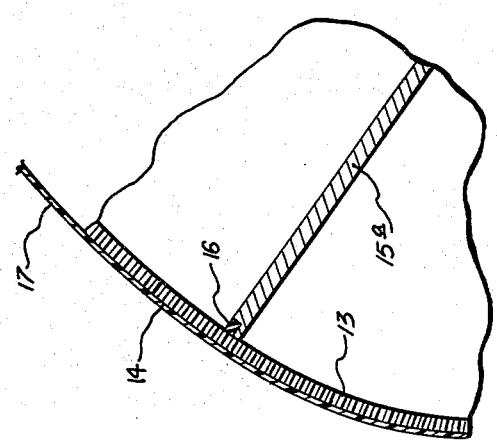
FIG. 2 is an enlarged, sectional view showing a segment of the forming surface as employed in the process; and, FIG. 3 is an enlarged, schematic, sectional view of a perforated film having tapered capillaries.

Referring to FIGS. 1 and 2, the vacuum chamber 15 is positioned within drum 10, along the axis of drum 10 and opens at the surface of the drum over a limited portion of its periphery in contact with the inner portion of surface 13 of drum 10. Two plates 15a define the chamber. In order to provide an effective seal of the leading and trailing edges of chamber 15, seals 16 are provided in plates 15a to form a seal against the surface 13. The seals may be made of rubber or other suitable material. The plates 15a are stationary and rigidly affixed to axle 11 or other suitable means so that chamber 15 remains in a fixed or stationary position in drum 10. Thus, chamber 15 is sealed at all points except the peripheral openings on drum 10 and may be evacuated or reduced in pressure by pumping equipment connected to the chamber in any suitable manner.

As can be seen in FIG. 1, located above and adjacent to drum 10 is extruder 21 which is used to extrude a hot thermoplastic sheet 17 onto drum 10. As the sheet material 17 travels downwardly from extruder 21, the sheet contacts screen 14 which is turning counter-clockwise with drum 10 in FIGS. 1 and 2. The rotating screen 14 carries sheet 17 over vacuum slot 15 which causes the thermoplastic material to be drawn into the openings in screen 14 and thereby perforated. The sheet 17 continues to travel around in a counter-clockwise manner shown in FIG. 1 on drum 10 and continues on to the rolls 19 and 20.

From roll 20 the sheet material 18 continues upwardly over roll 21 to corona treating roll 22. The corona treating roll 22 is usually covered with a suitable dielectric material such as epoxy, florinated polyethylene (TEFLON), chlorinated polyethylene (HYPALON), or polyester (MYLAR). The electrode or corona bar 23 is suspended parallel to the treater roll at about 1/16 of an inch above the roll. The corona bar 23 is energized by a transformer and corona treating power source 24. The sheet continues past a tension roll 25 to a second tension roll 26 and onto wind-up roll 27.

Figure 3:
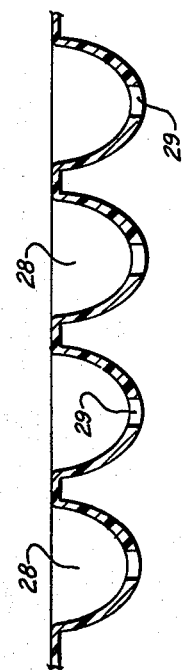

As can be seen in FIG. 3, the tapered capillaries 28 of the film have a hole 29 in the bottom thereof for release of liquids or fluids. The top or smooth side of the film is referred to as the female side and the bottom side of the film is referred to as the male side. The side walls in the preferred embodiment in FIG. 3 are shown to be curved, but they could be straight so that the capillaries would be conical.

The percentage run off is much lower in film that had been treated than in film which had not been treated. This improvement is especially significant in such applications as childrens' or adults' diapers where maximum liquid absorption is the goal.

The voltage and length of time of the corona treatment can vary according to the type of film being utilized. Composition of the film, the speed of the film through the treating unit, and thickness of the film can be varied to achieve the particular decrease in run off which is desired as a result of the treatment.

Preferably, the film prepared in accordance with the present invention have run off by volume of from 5 percent to 20 percent. The preferred film prepared in accordance with the present invention has a percentage run off of from 7 percent to 15 percent.

Any thermoplastic material which may be formed into flexible film or sheets may be used in the production of the novel products of the present invention. Exemplary thermoplastic materials include cellulose esters, e.g., cellulose acetate, cellulose propionate, cellulose butyrate; mixed esters of cellulose; cellulose ethers, e.g., ethyl cellulose; nylon and polymeric materials, e.g., polyvinyl alcohol acetals, polyvinyl chloride, polyvinyl chloride acetate, polystyral, methyl methacrylate, polyethylene, polypropylene, and other polyolefins which may be formed into flexible film or sheet, and the like. Particularly preferred perforated film are polyethylene and polypropylene. Sheets or film made from such materials may be plasticized with suitable plasticizers and other additives known in the art may be added to achieve the desired physical characteristics.

Although the preferred embodiments of the present invention have been disclosed and described in detail above, it should be understood that the invention is in no sense limited thereby and its scope is to be determined by that of the following claims.

What is claimed:

1. A process for increasing the liquid flow through perforated thermoplastic film having tapered capillaries, comprising:
   a. forming a perforated thermoplastic film having tapered capillaries; and,
   b. subjecting said perforated thermoplastic film having tapered capillaries to a corona discharge treatment sufficient to provide a perforated film having an increased liquid flow through rate over that of said perforated thermoplastic film prior to the corona discharge treatment and said film has a percent run off of from 5 percent to 20 percent.

2. The process of claim 1, wherein the tapered capillaries of said perforated thermoplastic film have curved side walls.

3. The process of claim 1 wherein the film has a run off percent of from 7 percent to 15 percent.

4. The process of claim 3 wherein said film is low density polyethylene.

5. The process of claim 3 wherein said film is polypropylene.

6. In a process for the preparation of perforated thermoplastic film having tapered capillaries, said process comprising forming a hot film of thermoplastic material, applying the hot film to a moving perforated screen, and applying an air pressure differential across the film toward a portion of the screen sufficient to distort the film into the perforations and cause rupture of the film, the improvement comprising subjecting said perforated film to a corona discharge treatment sufficient to provide a perforated film having an increased liquid flow through rate over that of said perforated thermoplastic film prior to the corona discharge treatment and said film has a percent run off of from 5 percent to 20 percent.

7. The process of claim 6 wherein the tapered capillaries of said perforated thermoplastic film have curved side walls.

8. The process of claim 6 wherein said film has a run off percent of from 7 percent to 15 percent.

9. The process of claim 8 wherein said film is low density polyethylene.

10. The process of claim 8 wherein said film is polypropylene.

* * * * *